United States Patent
Pan et al.

(10) Patent No.: US 11,125,684 B2
(45) Date of Patent: Sep. 21, 2021

(54) PLASMON WAVEGUIDE, BIOSENSOR CHIP AND SYSTEM

(71) Applicants: SHENZHEN INSTITUTE OF TERAHERTZ TECHNOLOGY AND INNOVATION, Shenzhen (CN); SHENZHEN INSTITUTE OF TERAHERTZ TECHNOLOGY AND INNOVATION CO., LTD., Shenzhen (CN)

(72) Inventors: Yi Pan, Shenzhen (CN); Qing Ding, Shenzhen (CN); Rongyue Liu, Shenzhen (CN); Chen Li, Shenzhen (CN)

(73) Assignees: SHENZHEN INSTITUTE OF TERAHERTZ TECHNOLOGY AND INNOVATION, Shenzhen (CN); SHENZHEN INSTITUTE OF TERAHERTZ TECHNOLOGY AND INNOVATION CO., LTD., Shenzhen (CN)

(*) Notice: Subject to any disclaimer, the term of this patent is extended or adjusted under 35 U.S.C. 154(b) by 0 days.

(21) Appl. No.: 16/629,524

(22) PCT Filed: Sep. 4, 2017

(86) PCT No.: PCT/CN2017/100396
§ 371 (c)(1),
(2) Date: Jan. 8, 2020

(87) PCT Pub. No.: WO2019/010774
PCT Pub. Date: Jan. 17, 2019

(65) Prior Publication Data
US 2021/0041356 A1 Feb. 11, 2021

(30) Foreign Application Priority Data
Jul. 12, 2017 (CN) .......................... 201710566845.0

(51) Int. Cl.
G01N 21/3577 (2014.01)
G01N 21/3581 (2014.01)
(Continued)

(52) U.S. Cl.
CPC ..... *G01N 21/3577* (2013.01); *G01N 21/3581* (2013.01); *G01N 21/553* (2013.01); *G01N 33/5302* (2013.01); *G01N 2201/0407* (2013.01)

(58) Field of Classification Search
CPC .......... G01N 21/3577; G01N 21/3581; G01N 21/553; G01N 21/55; G01N 33/5302; G01N 33/542
See application file for complete search history.

(56) References Cited

U.S. PATENT DOCUMENTS 10,459,257 B2 * 10/2019 Rupasinghe ............. A61N 5/06
2003/0059820 A1 * 3/2003 Vo-Dinh ............... C12Q 1/6837
506/3
(Continued)

FOREIGN PATENT DOCUMENTS

CN 102998242 A 3/2013
CN 104201443 A 12/2014
(Continued)

OTHER PUBLICATIONS

Clark et al. "Plasmonic Split-Ring Resonators as Dichroic Nanophotonic DNA Biosensors." J. Am. Chem. Soc. 131, 17615-17619. (Year: 2009).*

*Primary Examiner* — Michael C Bryant
(74) *Attorney, Agent, or Firm* — Maier & Maier, PLLC

(57) ABSTRACT

A plasmonic waveguide (10), a biosensor chip (100) and a system, wherein the plasmonic waveguide (10) is applied to the biosensor chip (100), and comprises a base (11) and a plasmonic structure (12) provided on the upper surface of the base (11); the plasmonic structure (12) comprises a plurality of plasmons (121) periodically arranged, the plasmons (121) being metal split rings, and the annular openings
(Continued)

of the plasmons (121) being used for fixing antibody probes (122). The plasmon waveguide (10) is provided in the biosensor chip (100), the target biomolecules in the detection liquid flowing into a microfluidic channel (31) can be captured by means of the antibody probes (122), and the plasmonic waveguide (10) is used to enhance the signal strength of terahertz waves emitted to the biosensor chip (100), thereby enhancing the signal strength of the reflected terahertz waves detected by a terahertz analyzer (300), improving the detection sensitivity, the signal-to-noise ratio and the reliability.

10 Claims, 3 Drawing Sheets

(51) Int. Cl.
*G01N 21/552* (2014.01)
*G01N 33/53* (2006.01)

(56) References Cited

U.S. PATENT DOCUMENTS

| | | | | |
|---|---|---|---|---|
| 2011/0017910 | A1* | 1/2011 | Nagel | G07D 7/06 |
| | | | | 250/338.4 |
| 2012/0257204 | A1* | 10/2012 | Walters | H01L 31/02327 |
| | | | | 356/445 |
| 2013/0252319 | A1* | 9/2013 | Jung | G01N 27/3276 |
| | | | | 435/287.2 |
| 2015/0253525 | A1* | 9/2015 | Hong | G01T 1/24 |
| | | | | 250/366 |

FOREIGN PATENT DOCUMENTS

| | | |
|---|---|---|
| CN | 104764711 A | 7/2015 |
| CN | 207020078 U | 2/2018 |

* cited by examiner

PLASMON WAVEGUIDE, BIOSENSOR CHIP AND SYSTEM

CROSS-REFERENCE TO RELATED APPLICATIONS

This application is a national stage entry under 35 U.S.C. 371 of PCT Patent Application No. PCT/CN2017/100396, filed Sep. 4, 2017, which claims priority to Chinese Patent Application No. 201710566845.0, filed Jul. 12, 2017, the entire contents of each of which is incorporated herein by reference.

TECHNICAL FIELD

Embodiments of the invention belong to the technical field of in-vitro diagnostics, and in particular, to a plasmonic waveguide, a biosensor chip, and a system.

BACKGROUND

In-vitro diagnostics technology collectively referred to as IVD (In-Vitro Diagnostics) technology in internation, refers to product and service that obtain clinical diagnostic information by detecting the blood and other tissues and secretions of human body in-vitro. Around the world, with the rise of new technologies and improvement of medical security policies, in-vitro diagnostics technology has become one of the fastest-growing trends in the bioengineering and pharmaceutical industry. In-vitro diagnostics technology and product have a short R&D cycle and a number of categories, and in addition to clinical application, they can also be extended to fields of food safety test, animal and plant disease monitoring etc., and are a focus for innovation and entrepreneurship in the field of biomedicine.

However, existing detection method for in-vitro diagnostics technology is usually based on traditional Turbidimetric inhibition immune assay or Real-time Quantitative PCR Detecting System (QPCR) technology with, and cannot meet increasing demand for in-vitro diagnostics technology due to low detection sensitivity, low detection speed and low reliability.

SUMMARY

Embodiment of the invention provides a plasmonic waveguide, a biosensor chip, and a system, which can enhance the terahertz wave signal and improve the detection sensitivity, signal-to-noise ratio and reliability of the biosensor chip.

One aspect of the embodiment of the invention provides a plasmonic waveguide applied to a biosensor chip, wherein the plasmonic waveguide comprises a base and a plasmonic structure provided on an upper surface of the base, the plasmonic structure comprises a plurality of plasmons arranged periodically, the plasmon is a metal split ring, and an annular opening of the plasmon is used for fixing an antibody probe. Herein, the plasmon refers to a structure of metal nanoparticles for plasma resonance.

In an embodiment, a horizontal periodic length and a vertical periodic length of the plasmonic structure are both 50 μm to 200 μm, an annular diameter of the plasmon is 30 μm to 100 μm, and a width of the annular opening is 10 nm to 2 μm.

In an embodiment, the metal split ring is a circular split ring, an elliptical split ring or a polygon split ring.

In an embodiment, the base is a silicon base, a glass base, or a plastic base.

In an embodiment, the plasmon is prepared by 3D printing technology or ultraviolet lithography technology, and the plasmon is attached to the upper surface of the base by a metal electrodeposition process to form the plasmonic structure.

Another aspect of the embodiment of the invention further provides a biosensor chip, which comprises a detection liquid preprocessing chip and a microfluidic chip bonded to a same substrate, wherein the microfluidic chip comprises at least one microfluidic channel, and the above-mentioned plasmonic waveguide is disposed within the microfluidic channel;

the detection liquid preprocessing chip comprises a detection liquid inlet and a detection liquid outlet whose number is equal to the number of the at least one microfluidic channel, and an inlet of each microfluidic channel is correspondingly connected to one detection liquid outlet;

a detection liquid sample flows from the detection liquid inlet, and is processed by the detection liquid preprocessing chip to obtain a detection liquid, the detection liquid flows into the microfluidic channel through the detection liquid outlet and the inlet, target biomolecules in the detection liquid are captured by the antibody probe on the plasmonic waveguide in the microfluidic channel, and the at least one microfluidic channel captures at least one type of target biomolecules in the detection liquid.

In an embodiment, the antibody probes on the plasmonic waveguides in each microfluidic channel are the same as each other, and the at least one microfluidic channel captures a same type of target biomolecule in the detection liquid.

In an embodiment, the test fluid sample is a blood sample.

In an embodiment, the connection between the inlet and the detection liquid outlet correspondingly connected is sealed by polydimethylsiloxane.

Still another aspect of the embodiment of the invention further provides a biosensor system, which comprises the above-mentioned biosensor chip, and further comprises a terahertz source and a terahertz analyzer; wherein the terahertz source is configured to emit a terahertz wave to the biosensor chip capturing the target biomolecules, the terahertz analyzer is configured to receive the terahertz wave reflected by the biosensor chip and perform terahertz spectrum analysis on the reflected terahertz wave to detect biological characteristics of the target biomolecules captured by the biosensor chip.

In an embodiment of the invention, by providing the plasmonic waveguide within the biosensor chip, the target biomolecules in the detection liquid flowing into a microfluidic channel can be captured by means of the antibody probes, and the plasmonic waveguide is used to enhance the signal strength of terahertz waves emitted to the biosensor chip, thereby enhancing the signal strength of the reflected terahertz waves detected by a terahertz analyzer, improving the detection sensitivity, the signal-to-noise ratio and the reliability.

BRIEF DESCRIPTION OF THE DRAWINGS

In order to more clearly illustrate the technical solutions in the embodiments of the invention, the drawings to be used in the description of the embodiments are briefly introduced below; obviously, the drawings in the following description are some embodiments of the invention, and those of ordinary skilled in the art can obtain other drawings according to these drawings without paying creative effort.

DETAILED DESCRIPTION OF EMBODIMENTS

In order to enable those skilled in the art to better understand the solutions of the invention, the technical solutions in the embodiments of the invention will be clearly described below in conjunction with the drawings in the embodiments of the invention; obviously, the described embodiments are a part of the embodiment of the invention, rather than all embodiments. Based on the embodiments in the invention, all other embodiments obtained by those of ordinary skilled in the art without paying creative effort shall fall within the protection scope of the invention.

The terms "comprise" and "include" and any variants thereof in the description and Claims and the above-mentioned drawings of the invention are intended to encompass non-exclusive inclusion. For example, a process, method, or system, product, or apparatus containing a series of steps or units are not limited to the listed steps or units, but optionally also include steps or units not listed, or optionally include other steps or units inherent to the process, method, product or apparatus. In addition, the terms "first", "second", "third", and the like are used to distinguish different objects and are not used to describe specific orders.

Figure 1:
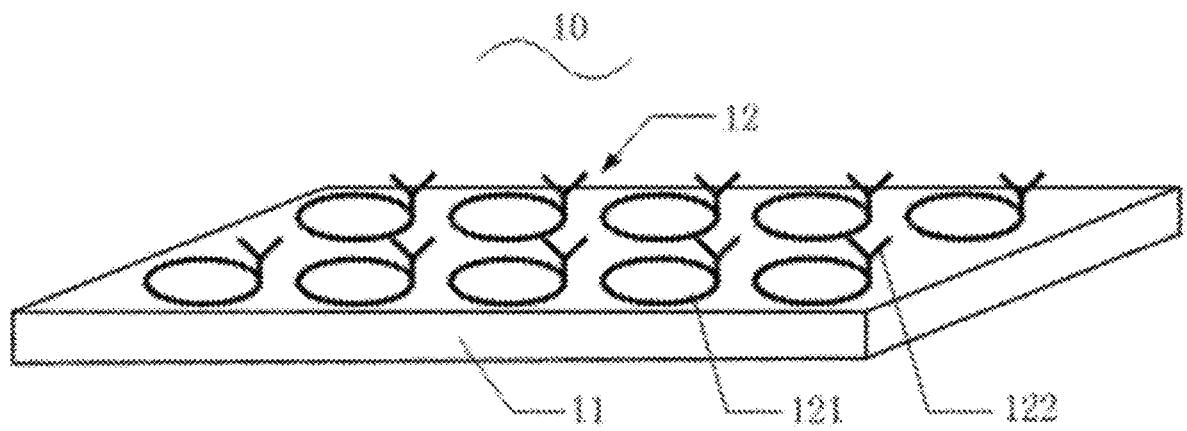
FIG. 1 is a schematic diagram of a basic structure of a plasmonic waveguide provided by an embodiment of the invention.

As shown in FIG. 1, an embodiment of the invention provides a plasmonic waveguide 10 applied to a biosensor chip, which includes a base 11 and a plasmonic structure 12 provided on an upper surface of the base 11 The plasmonic structure 12 includes a plurality of plasmons 121 arranged periodically The plasmon is a metal split ring, and an annular opening of the plasmon 121 is used for fixing an antibody probe 122.

In a specific application, the metal split ring is a circular split ring, an elliptical split ring or a polygon split ring.

Figure 2:
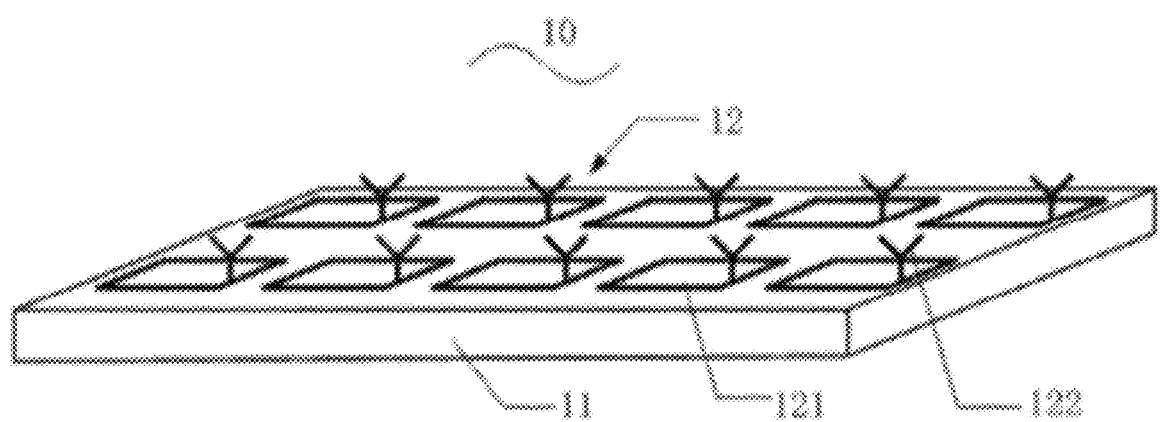
FIG. 2 is a schematic diagram of a basic structure of a plasmonic waveguide provided by another embodiment of the invention.

FIG. 1 exemplarily shows that the plasmon 121 is a circular split ring, and FIG. 2 exemplarily shows that the plasmon 121 is a square split ring.

In a specific application, the number, size, and arrangement rule of plasmons included in the plasmonic structure can be set according to actual needs, for example, all plasmons on the plasmonic structure can be regularly arranged in a rectangular array, a circular array, or any polygon array, etc.

FIGS. 1 and 2 exemplarily show that the plasmons 121 on the plasmonic structure 12 are regularly arranged in a matrix array.

In an embodiment, a horizontal periodic length and a vertical periodic length of the plasmonic structure are both 50 μm to 200 μm, an annular diameter of the plasmon is 30 μm to 100 μm, and a width of the annular opening is 10 nm to 2 μm.

In a specific application, the horizontal direction specifically refers to arrangement direction of any row of plasmons, and the vertical direction refers to arrangement direction of any column of plasmons perpendicular to the horizontal direction, and the horizontal periodic length and vertical periodic length can be the same or different The annular diameter refers to annular outer diameter of the plasmon. When the plasmon is a circular split ring, the annular diameter refers to an diameter of the outer ring of the circular split ring; when the plasmon is an elliptical split ring, the annular diameter refers to the longer diameter of the outer ring of the elliptical split ring; and when the plasmon is a square split ring, the annular diameter refers to side length of the outer ring of the square split ring.

In an embodiment, the horizontal periodic length and vertical periodic length of the plasmonic structure are both 50 μm, and the annular diameter of the plasmon is 36 μm.

In an embodiment, the horizontal periodic length of the plasmonic structure is 40 μm, the vertical periodic length of the plasmonic structure is 60 μm, and the annular diameter of the plasmonic structure is 36 μm.

In a specific application, the base can be made of any type of material according to actual need, and in an embodiment, the base is a silicon base, a glass base, or a plastic base.

In a specific application, the plasmon can be prepared by 3D printing technology or ultraviolet lithography technology, and the plasmon can be attached to the upper surface of the base by a metal electrodeposition process to form the plasmonic structure.

In a specific application, depending on the type of target biomolecule to be captured, antibody probes of different types can be fixed at the annular opening of the plasmon, for example, if tumor cell antigens are to be captured, tumor cell antibody probes are is fixed.

In this embodiment, by providing the above-mentioned plasmonic waveguide within the biosensor chip, the target biomolecules in the detection liquid flowing into a microfluidic channel can be captured by means of the antibody probes, and the plasmonic waveguide is used to enhance the signal strength of terahertz waves emitted to the biosensor chip, thereby enhancing the signal strength of the reflected terahertz waves detected by a terahertz analyzer, improving the detection sensitivity, the signal-to-noise ratio and the reliability.

Figure 3:
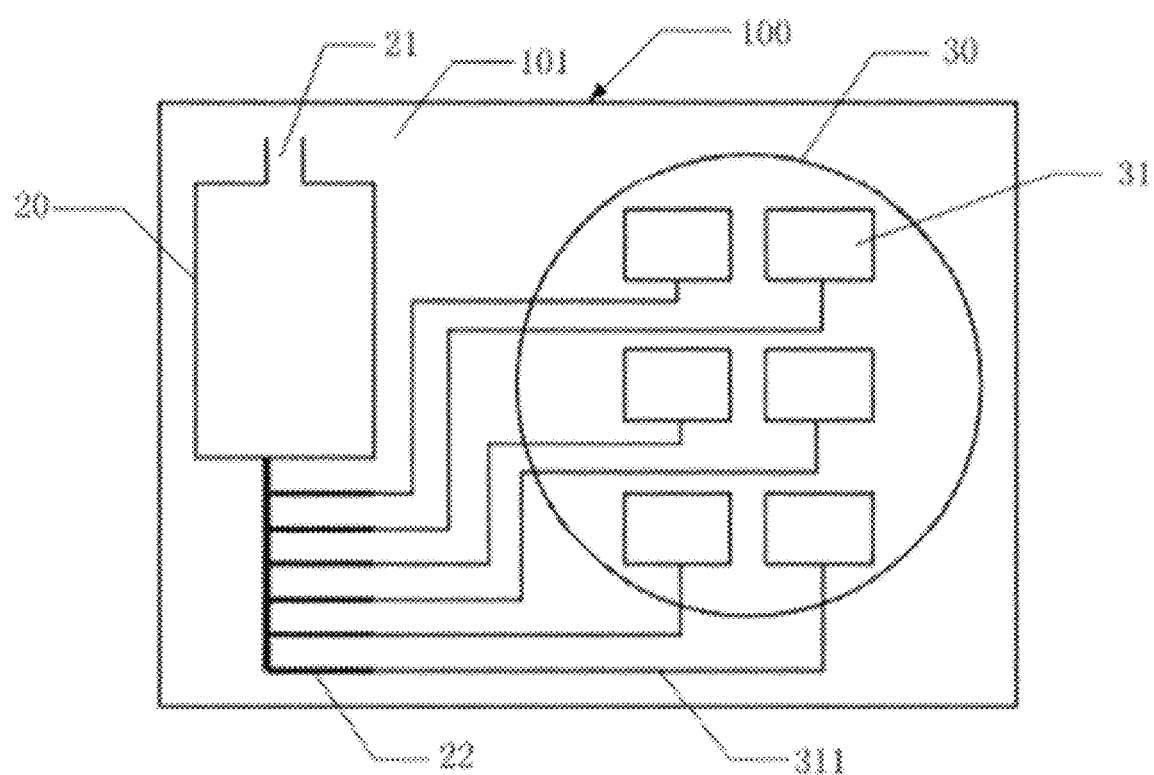
FIG. 3 is a schematic diagram of a basic structure of a biosensor chip according to an embodiment of the invention.

As shown in FIG. 3, an embodiment of the invention provides a biosensor chip 100 implemented based on a plasmonic waveguide 10, and the biosensor chip includes a detection liquid preprocessing chip 20 and a microfluidic chip 30 bonded to a same substrate 101, the microfluidic chip 30 includes at least one microfluidic channel 31, and a plasmonic waveguide 10 is disposed within the microfluidic channel 31.

The detection liquid preprocessing chip 20 includes a detection liquid inlet 21 and a detection liquid outlet 22 whose number is equal to the number of the at least one microfluidic channel 31, and an inlet 311 of each microfluidic channel 31 is correspondingly connected to one detection liquid outlet 22.

In a specific application, the substrate may specifically be a glass substrate or a silicon substrate.

In an embodiment, the connection between the inlet and the detection liquid outlet correspondingly connected is sealed by polydimethylsiloxane.

The working principle of the biosensor chip provided by this embodiment is as follows:

a detection liquid sample flows from the detection liquid inlet, and is processed by the detection liquid preprocessing chip to obtain the detection liquid, the detection liquid flows into the microfluidic channel through the detection liquid outlet and the inlet. The target biomolecule in the detection liquid is captured by the antibody probe on the plasmonic waveguide in the microfluidic channel, and the at least one microfluidic channel captures at least one type of target biomolecule in the detection liquid.

In a specific application, the detection liquid sample may be blood, tissue fluid, or secretion, etc.

In an embodiment, the detection liquid sample is blood.

FIG. 3 exemplarily shows that the microfluidic chip 30 includes 6 microfluidic channels 31, and for convenience of illustration, the plasmonic waveguide is not labeled in FIG. 3.

Based on the biosensor chip 100 shown in FIG. 3, 1 to 6 types of target biomolecules can be captured, which is specifically determined by the type of antibody probes on the plasmonic waveguides in 6 microfluidic channels. If the antibody probes on the plasmonic waveguides in 6 microfluidic channels are all the same, only 1 type of target biomolecule can be captured at the same time; if they are different from each other, 6 types of target biomolecules can be captured; if two of them are the same and the other four are different, 5 types of target biomolecules can be captured, and so on.

In an embodiment, the antibody probes on the plasmonic waveguides in each microfluidic channel are all the same, and the at least one microfluidic channel captures the same type of target biomolecule in the detection liquid.

In a specific application, when all the microfluidic channels are used to capture the same type of target biomolecule at the same time, detection precision of the target biomolecule in the detection liquid can be effectively improved, and reliability of the detection result of the biosensor chip can be improved.

In a specific application, a microfluidic chip is formed by bonding at least one microfluidic channel and a glass substrate.

In this embodiment, the detection liquid preprocessing chip is used to preprocess the detection liquid sample, cells or particles in the detection liquid that do not need to be detected can be filtered or entrapped, a relatively pure detection liquid containing the target biomolecule is obtained, which is convenient for subsequent analysis and capture of target biomolecule in the microfluidic channel; by providing a microfluidic chip including at least one microfluidic channel, at least one target biomolecule can be captured, and detection efficiency and detection reliability can be improved.

Figure 4:
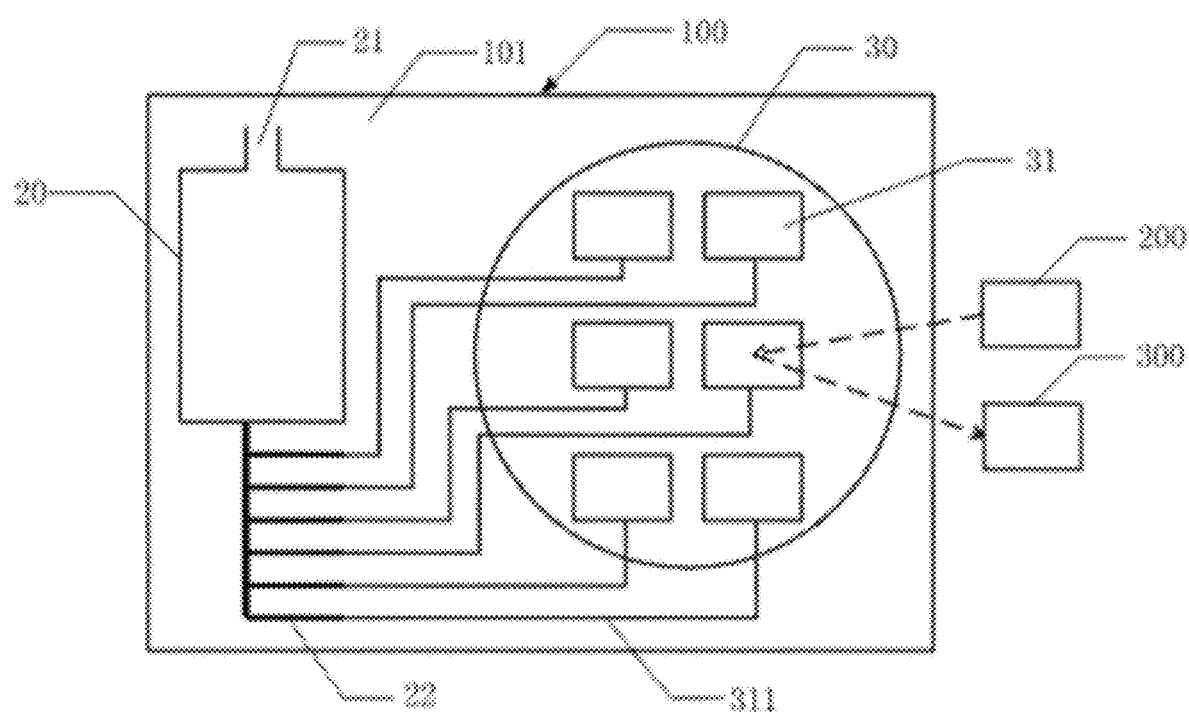
FIG. 4 is a schematic diagram of a basic structure of a biosensor system according to an embodiment of the invention.

As shown in FIG. 4, an embodiment of the invention provides a biosensor system, which includes a biosensor chip 100, and further includes a terahertz source 200 and a terahertz analyzer 300.

The terahertz source emits a terahertz wave to the biosensor chip that capturing the target biomolecule; the terahertz analyzer receives the terahertz wave reflected by the biosensor chip and performs terahertz spectrum analysis on the reflected terahertz wave to detect the biological characteristics of target biomolecule captured by the biosensor chip.

In a specific application, the biological characteristics of target biomolecule include number, size, and cell structure, etc.

The above description is only the preferred embodiments of the invention and is not intended to limit the invention, any modification, equivalent substitution, and improvement made within the spirit and principle of the invention shall be included in the scope of the invention.

What is claimed is:

1. A plasmonic waveguide for a biosensor chip, wherein the plasmonic waveguide comprises a base and a plasmonic structure provided on an upper surface of the base, the plasmonic structure comprises a plurality of plasmons arranged periodically, each of the plurality of plasmons is a metal split ring with an annular opening configured to fix an antibody probe, and
   a horizontal periodic length and a vertical periodic length of the plurality of plasmons are both 50 µm to 200 µm.

2. The plasmonic waveguide according to claim 1, wherein a horizontal periodic length and a vertical periodic length of the plurality of plasmons are both 50 µm to 200 µm an annular diameter of each of the plurality of plasmons is 30 µm to 100 µm and a width of the annular opening is 10 nm to 2 µm.

3. The plasmonic waveguide according to claim 1, wherein the metal split ring is a circular split ring, an elliptical split ring or a polygon split ring.

4. The plasmonic waveguide according to claim 1, wherein the base is a silicon base, a glass base, or a plastic base.

5. The plasmonic waveguide according to claim 1, wherein each of the plurality of plasmons is configured to be prepared by 3D printing technology or ultraviolet lithography technology, and to be attached to the upper surface of the base by a metal electrodeposition process to form the plasmonic structure.

6. A biosensor chip comprising a detection liquid preprocessing chip and a microfluidic chip bonded to a same substrate, wherein the microfluidic chip comprises at least one microfluidic channel, and the plasmonic waveguide according to claim 1 is disposed within the microfluidic channel;
   the detection liquid preprocessing chip comprises a detection liquid inlet and a detection liquid outlet whose number is equal to the number of the at least one microfluidic channel, and an inlet of each microfluidic channel is correspondingly connected to one detection liquid outlet;
   the detection liquid preprocessing chip is configured to process a detection liquid sample flowing from the detection liquid inlet to obtain a detection liquid; and
   the at least one microfluidic channel is configured to capture at least one type of target biomolecules in the detection liquid by antibody probes fixed on the plasmonic waveguide in the microfluidic channel, when the detection liquid flows into the microfluidic channel through the detection liquid outlet and the inlet.

7. The biosensor chip according to claim 6, wherein the antibody probes fixed on the plasmonic waveguide in each microfluidic channel are the same as each other, and the at least one microfluidic channel is configured to captures a same type of target biomolecules in the detection liquid.

8. The biosensor chip according to claim 6, wherein the detection liquid sample is a blood sample.

9. The biosensor chip according to claim 6, wherein the connection between the inlet and the detection liquid outlet correspondingly connected is sealed by polydimethylsiloxane.

10. A biosensor system, comprising the biosensor chip according to claim 6, a terahertz source and a terahertz analyzer; wherein
   the terahertz source is configured to emit a terahertz wave to the biosensor chip capturing the target biomolecules, the terahertz analyzer is configured to receive the terahertz wave reflected by the biosensor chip and perform terahertz spectrum analysis on the reflected terahertz wave to detect biological characteristics of the target biomolecules captured by the biosensor chip.

* * * * *